US005322770A

United States Patent [19]

Gelfand

[11] Patent Number: 5,322,770
[45] Date of Patent: * Jun. 21, 1994

[54] REVERSE TRANSCRIPTION WITH THERMOSTABLE DNA POLYMERASES - HIGH TEMPERATURE REVERSE TRANSCRIPTION

[75] Inventor: David H. Gelfand, Oakland, Calif.

[73] Assignee: Hoffman-LaRoche Inc., Nutley, N.J.

[ * ] Notice: The portion of the term of this patent subsequent to May 10, 2011 has been disclaimed.

[21] Appl. No.: 455,611

[22] Filed: Dec. 22, 1989

[51] Int. Cl.$^5$ .................. C12P 19/34; C12Q 1/68; C07H 5/04; C07H 15/12

[52] U.S. Cl. .................. 435/6; 435/91.51; 435/7.91; 435/91.2; 435/91.21; 536/16.7; 536/25.6; 935/77; 935/73

[58] Field of Search ............ 435/6, 91, 172.3, 7.91; 536/18.7, 25.6; 935/77, 78

[56] References Cited

U.S. PATENT DOCUMENTS 4,683,202  7/1987  Mullis .................. 435/91
4,889,818  12/1989  Gelfand et al. .............. 435/194

FOREIGN PATENT DOCUMENTS 258017  3/1988  European Pat. Off. .
359006  3/1990  European Pat. Off. .

OTHER PUBLICATIONS

Chien et al J. of Bart. 127(3)1550 (1976).
Karkas J. P.N.A.S. 70(12)PII:3834 (1973).
Karkas, 1973, Proc. Natl. Acad. Sci. USA 70(12):3834–3838.
Loeb et al., 1973, Nature New Biol. 242:66–69.
Gulati et al., 1974, Proc. Natl. Acad. Sci. USA 71(4):1035–1039.
Shimomaye and Salvato, 1989, Gene Anal Techn. 6:25–28.
Tse and Forget, 1990, Gene 88:293–296.
Shaffer et al., 1990, Analytical Biochemistry 190-292-296.
Ruttimann et al., 1985, Eur. J. Biochem. 149:41–46.
Brown, Basic Principles in Nucleic Acid Chemistry 2:43–44, New York, Academic Press.
Houdebine, 1976, "Synthesis of DNA Complementary to the mRNAs for Milk Proteins by *E. coli* DNA Polymerase I" Nucleic Acids Research 3(3):615–630.
Karkas et al., 1972, "Action of DNA Polymerase I of *Escherichia coli* with DNA–RNA Hybrids as Templates" Proc. Natl. Acad. Sci. USA 69(2):398–402.
"Metal Ions in Genetic Information Transfer" in Advances in Inorganic Biochemistry vol. 3, p. 27 published by Elsevier North Holland Inc. New York, N.Y. Eds. Eichorn, Gunther, Louis and Marzill, Luigi, 1981.
Mizutani and Temin, 1976, "Incorporation of Noncomplementary Nucleotides at High Frequencies by Ribodeoxyvirus DNA Polymerases and *Escherichia coli* DNA Polymerase I" Biochemistry 15:1510–1516.
Temin and Mizutani, Chapter 7, Entitled "RNA Tumor Virus DNA Polymerases", The Enzymes, Paul Boyer, Academic Press, Inc. London, 1974 ed.
Travaglina and Leob, 1974, "Ribonucleic Acid Dependent Deoxyribonucleic Acid Synthesis by *Escheichia coli* Deoxyribonucleic Acids Polymerase I Characterization of the Polymerization Reaction" Biochemistry 13(15):3010–3017.
Travaglina et al., 1976, "Template Recognition and Chain Elongation in DNA Synthesis in Vitro" J. Mol. Biol. 106:605–621.
Chien et al., 1976, *J. Bacteriology* 127(3):1550–1557.
Kaledin et al., 1980, *Biokhimiya* 45(4):644–651.
Lawyer et al., 1989, *J. Biol. Chem.* 264(11):6427–6437.
Tabor and Richardson, 1989, *Proc. Natl. Acad. Sci. USA* 86:4076–4080.
Kawasaki, "Amplification of RNA Sequences via Complementary DNA (RNA)".
Jones and Foulkes, 1989, *Nucleic Acids Research* 17(20):8387–8388.

Primary Examiner—Robert A. Wax
Assistant Examiner—Miguel Escallon
Attorney, Agent, or Firm—George M. Gould; Dennis P. Tramaloni; Stacey RG351.5 Sias

[57] ABSTRACT

Methods are provided for the replication and amplification of RNA sequences by thermostable DNA polymerases. Reverse transcription of RNA is catalyzed by, for example, 92 kDa Taq, 64 kDa Taq, and Tth DNA polymerase. Reverse transcription is coupled to PCR amplification in a one enzyme procedure using a thermostable polymerase.

18 Claims, 2 Drawing Sheets

REVERSE TRANSCRIPTION WITH THERMOSTABLE DNA POLYMERASES - HIGH TEMPERATURE REVERSE TRANSCRIPTION

FIELD OF THE INVENTION

The present invention relates to the field of molecular biology and provides improved methods for the replication and amplification of ribonucleic acid (RNA) sequences. In a preferred embodiment, the invention provides a method for synthesizing a DNA transcript from an RNA template with a thermostable DNA polymerase.

BACKGROUND OF THE INVENTION

The term "reverse transcriptase" describes a class of polymerases characterized as RNA dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

Avian myoblastosis virus (AMV) reverse transcriptase was the first widely used RNA dependent DNA polymerase (Verma, 1977, *Biochem. Biophys. Acta* 473:1). The enzyme has both a 5'-3' RNA directed DNA polymerase activity as well as an RNAseH activity. RNAseH is a processive 5' and 3' riboexonuclease specific for the RNA strand of RNA-DNA hybrids (Perbal, 1984, *A Practical Guide to Molecular Cloning*, Wiley & Sons New York). Errors in transcription cannot be corrected by reverse transcriptase (Saunders and Saunders, 1987, *Microbial Genetics Allied to Biotechnology*, Croom Helm, London). A detailed study of the activity of AMV reverse transcriptase and its associated ribonuclease H has been presented by Berger et al., 1983, *Biochemistry* 22:2365-2372.

Berger et al. found that the rate limiting step in RNA transcription was initiation of the transcription reaction, rather than the sequential polymerization of additional nucleotides. To overcome this limitation, use of a stoichiometric, rather than catalytic, quantity of reverse transcriptase is frequently recommended (Buell et al., 1978, *J. Biol. Chem.* 253:2471-2482; Wickens et al., 1978, *J. Bio. Chem.* 253:2483-2495; Yoo et al., 1982, *Proc. Nat. Acad. Sci. USA* 80:1194-1198; and Okayama and Berg, 1982, *Mol. Cell. Biol.* 2:161-170). However, when stoichiometric amounts of reverse transcriptase are used, the low level of RNAseH activity is significant and may be responsible for fragmented cDNAs and limited cDNA yields. Christopher et al., 1980, *Eur. J. Biochem.* 111:4190-4231, and Michelson et al., 1983, *Proc. Nat. Acad. Sci. USA* 80:472-476, have suggested that including an RNAse inhibitor in cDNA reactions could alleviate this problem.

DNA polymerases isolated from mesophilic microorganisms such as *E. coli*. have been extensively researched (see, for example, Bessman et al., 1957, *J. Biol. Chem.* 233:171-177 and Buttin and Kornberg, 1966, *J. Biol. Chem.* 241:5419-5427). *E. coli* DNA polymerase I (Pol I) is useful for a number of applications including: nick-translation reactions, DNA sequencing, in vitro mutagenesis, second strand cDNA synthesis, polymerase chain reactions (PCR), and blunt end formation for linker ligation (Maniatis et al., 1982, *Molecular Cloning: A Laboratory Manual* Cold Spring Harbor, N.Y.).

Several laboratories have shown that some DNA polymerases are capable of in vitro reverse transcription of RNA (Karkas, 1973, *Proc. Nat. Acad. Sci. USA* 70:3834-3838; Gulati et al., 1974, *Proc. Nat. Acad. Sci. USA* 71:1035-1039; and Wittig and Wittig, 1978, *Nuc. Acid Res.* 5:1165-1178). Gulati et al. found that *E. coli* Pol I could be used to transcribe $Q\beta$ viral RNA using oligo(dT)$_{10}$ as a primer. Wittig and Wittig have shown that *E. coli* Pol I can be used to reverse transcribe tRNA that has been enzymatically elongated with oligo(dA). However, as Gulati et al. demonstrated, the amount of enzyme required and the small size of the cDNA product suggests that the reverse transcriptase activity of *E. coli* Pol I has little practical value.

The thermostable DNA polymerase from *Thermus aquaticus* (Taq) has been cloned, expressed, and purified from recombinant cells (Lawyer et al., 1989, *J. Biol. Chem.* 264:6427-6437 and European patent publication EP 258,017, incorporated herein by reference). Crude preparations of a DNA polymerase activity isolated from *T. aquaticus* have been described by others (Chien et al., 1976, *J. Bacteriol.* 127:1550-1557, and Kaledin et al., 1980, *Biokymiya* 45:644-651).

Taq polymerase, a 94 kDa enzyme, has a 75° C. temperature optimum activity. The enzyme is not permanently inactivated even when heated to 93°-95° C. for brief periods of time, as, for example, in the practice of DNA amplification by the polymerase chain reaction (PCR). In contrast, at this elevated temperature *E. coli* DNA Pol I and reverse transcriptases are inactivated.

Like *E. coli* Pol I, Taq polymerase requires a primer for initiation of synthesis; however, the thermostable properties of Taq are advantageous for extension of a DNA primer on a DNA template. Enhanced specificity of primer binding at elevated temperatures results in a higher yield of the desired product with less nonspecific product. When used in PCR, Taq needs to be added only at the beginning of the reaction rather than before each round of amplification, as is necessary when using *E. coli* Pol I. PCR methods for amplifying and detecting DNA sequences are disclosed in U.S. Pat. Nos. 4,683,195, 4,683,202, and 4,800,159, incorporated herein by reference.

PCR requires a nucleic acid template and appropriate primers for amplification. The DNA to be amplified may be synthetic or genomic, contained in a plasmid, or contained in a heterogenous sample. If the nucleotide sequence to be amplified is RNA, the nucleic acid molecule is first treated with reverse transcriptase in the presence of a primer to provide a cDNA template for amplification. Prior to the present invention, amplification of RNA necessitated a reverse transcription step with, e.g., non-thermostable reverse transcriptases such as AMVRT, followed by treatment of the resulting cDNA with a DNA polymerase. The amplification of RNA could be greatly simplified by the availability of a method for reverse transcribing RNA and amplifying DNA with a single enzyme.

The present invention addresses this need. The present invention provides methods for the efficient amplification of RNA sequences requiring only one enzyme, a thermostable DNA polymerase. These methods offer simplicity and enhanced specificity over currently known methods.

SUMMARY OF THE INVENTION

In one aspect, the present invention provides a method for reverse transcribing an RNA template, the method comprising the steps of: (a) adding a primer to a sample containing said RNA, under conditions whereby the primer will anneal to the RNA template providing an annealed primer-RNA template; and (b) treating the annealed primer-RNA template with a thermostable DNA polymerase in the presence of all four deoxyribonucleotide triphosphates in an appropriate buffer and at a temperature sufficient for said thermostable DNA polymerase to catalyze the polymerization of the deoxyribonucleotide triphosphates to form a DNA sequence complementary to the sequence of the RNA.

In another aspect, the present invention provides a method for amplifying an RNA template, the method comprising the steps of: (a) adding a first primer to a sample containing RNA, under conditions such that the primer will anneal to the RNA template providing an annealed primer-RNA template; (b) treating the annealed primer-RNA template with a thermostable DNA polymerase in the presence of all four deoxyribonucleotide triphosphates and appropriate buffers at a temperature sufficient for said thermostable DNA polymerase to catalyze the polymerization of deoxyribonucleotide triphosphates to form a cDNA sequence complementary to the sequence of the RNA; (c) treating the cDNA formed in step (b) to provide single-stranded cDNA; (d) annealing said single-stranded cDNA formed in step (c) to a second primer, wherein said second primer can hybridize to at least one single-stranded cDNA molecule and initiate synthesis of an extension product; (e) treating said primer-cDNA template with said thermostable DNA polymerase to produce a double-stranded cDNA molecule; and (f) amplifying the double-stranded cDNA molecule of step (e) by a polymerase chain reaction.

In another aspect, the present invention provides a method for detecting a specific target RNA sequence in a biological sample, the method comprising the steps of: (a) adding a primer to a sample suspected of containing a specific target RNA, said primer comprising sequence complementary to a sequence contained within said target RNA whereby the primer will anneal to said specific target RNA template if present in the sample; (b) treating the annealed primer-RNA template with a thermostable DNA polymerase in the presence of all four deoxyribonucleotide triphosphates in an appropriate buffer and at a temperature sufficient for said thermostable DNA polymerase to catalyze the polymerization of a DNA sequence complementary to a sequence contained within the target RNA; (c) treating the cDNA formed in step (b) to provide single-stranded cDNA; (d) repeating said step (b) and said step (c) at least once; and (e) determining whether amplification has occurred.

DETAILED DESCRIPTION OF THE INVENTION

The present invention provides improved methods for transcribing and amplifying RNA. These improvements are achieved by the discovery and application of previously unknown properties of thermostable DNA polymerases. The methods provide a one enzyme procedure for reverse transcribing and amplifying any desired RNA target and replace prior methods requiring more than one enzyme.

The methods comprise the steps of (a) combining an RNA template with a suitable primer under conditions whereby the primer will anneal to the corresponding RNA template; and (b) reverse transcribing the RNA template by incubating the annealed primer-RNA template mixture with a thermostable DNA polymerase and under conditions sufficient for the thermostable DNA polymerase to catalyze the polymerization of deoxyribonucleotide triphosphates to form a DNA sequence complementary to the sequence of the RNA template.

In another aspect, a primer suitable for annealing to an RNA template may also be suitable for amplification by PCR. For PCR, a second primer, complementary to the reverse transcribed cDNA strand, provides a site for initiation of synthesis of an extension product. As is well known, the thermostable DNA polymerase is able to catalyze this extension reaction on the DNA as template; however, until the present invention, no one recognized that the enzyme could also catalyze the RNA reverse transcription reaction. In the amplification of an RNA molecule by a thermostable DNA polymerase, the first extension reaction is reverse transcription and a DNA strand is produced. The second extension reaction, using the DNA template, produces a double-stranded DNA molecule. Thus, synthesis of a complementary DNA strand from an RNA template by a thermostable DNA polymerase provides the starting material for amplification.

The invention provides simplified and improved methods for the detection of RNA target molecules in a sample. These methods employ thermostable DNA polymerases to catalyze reverse transcription, second strand cDNA synthesis, and, if desired, amplification by PCR. Thus, the invention provides methods which require only one enzyme where previous methods required two. Prior methods also required two sets of incubation conditions, necessitated by the use of different enzymes for each procedure. The methods of the present invention provide RNA transcription and amplification with enhanced specificity and with fewer steps than previous RNA cloning and diagnostic methods. These methods are adaptable for use in kits for laboratory or clinical analysis.

The present invention is suitable for transcribing and amplifying RNA from a number of sources. The RNA template may be contained within a nucleic acid preparation from an organism, for example, a viral or bacterial nucleic acid preparation. The preparation may be a preparation containing cell debris and other components, purified total RNA, or purified mRNA. The RNA template may be a population of heterogeneous RNA molecules in a sample. Thus, the invention provides methods wherein a mixed population of mRNA molecules is reverse transcribed by a thermostable DNA polymerase when, for example, oligo(dT) is used as a primer.

RNA suitable for use in the present methods may be contained in a biological sample suspected of containing a specific target RNA. The biological sample may be a heterogenous sample in which RNA is a small portion of the sample, as in for example, a blood sample or a biopsied tissue sample. Thus, the method is useful for clinical detection and diagnosis.

In an illustrative embodiment, the RNA template is synthesized in vitro by T7 RNA polymerase transcription from a DNA template. The resulting RNA molecule, referred to as cRNA, may be purified by various means including gel electrophoresis or oligo(dT) chromatography.

The first step of the present method requires that the RNA template is combined with a suitable primer. As used herein the term "primer" refers to an oligonucleotide capable of acting as a point of initiation of DNA synthesis when annealed to a nucleic acid template under conditions in which synthesis of a primer extension product is initiated, i.e., in the presence of four different nucleotide triphosphates and a thermostable enzyme in an appropriate buffer ("buffer" includes pH, ionic strength, cofactors, etc.) and at a suitable temperature. A suitable primer useful in step (a) of the disclosed methods can hybridize to an RNA template. The primer may be an oligodeoxyribonucleotide such as oligo(dT). The primer is sufficiently long to prime the synthesis of extension products in the presence of the thermostable enzyme.

The primer typically contains 10-30 nucleotides, although that exact number is not critical to the successful application of the method. Short primer molecules generally require cooler temperatures to form sufficiently stable hybrid complexes with the template. In the disclosed embodiment of the present invention the primer is a DNA primer 24 bases in length and contains a nucleotide sequence complementary to a portion of the nucleotide sequence present in the mRNA molecule encoding the human cytokine interleukin-1-beta (IL-1β).

Hybridization of primer to the RNA template requires annealing conditions. Not every nucleotide of the primer must anneal to the template for reverse transcription to occur. The primer sequence need not reflect the exact sequence of the template. For example, a non-complementary nucleotide fragment may be attached to the 5' end of the primer with the remainder of the primer sequence being complementary to the RNA. Alternatively, non-complementary bases can be interspersed into the primer, provided that the primer sequence has sufficient complementarity with the RNA template for hybridization to occur and allow synthesis of a complementary DNA strand.

Annealing may be accomplished by various means. Destabilization of secondary and tertiary structure of the RNA template may be required to allow the primer to hybridize to the RNA. Examples of annealing means include incubating the RNA/primer mixture at a high temperature for a short period of time followed by either step-wise cooling or quick chilling the mixture in a dry ice/ethanol bath, or adding a chemical denaturant, such as methyl mercury, to the RNA/primer mixture. Annealing is routinely accomplished in the presence of an annealing buffer. Maniatis et al. (supra) provide examples of annealing buffers.

The present methods provide that the reverse transcription of the annealed primer-RNA template is catalyzed by a thermostable DNA polymerase. As used herein, the term "thermostable polymerase" refers to an enzyme that is heat stable or heat resistant and catalyzes polymerization of deoxyribonucleotides to form primer extension products that are complementary to a nucleic acid strand. Thermostable DNA polymerases useful herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90°-100° C. under polymerization conditions.

Of course, it will be recognized that for the reverse transcription of mRNA, the template molecule is single-stranded and therefore, a high temperature denaturation step is unnecessary. A first cycle of primer elongation provides a double-stranded template suitable for denaturation and amplification as referred to above.

The heating conditions will depend on the buffer, salt concentration, and nucleic acids being denatured. Temperatures for RNA destabilization typically range from 50°-80° C. Temperatures for nucleic acid denaturation typically range from about 90° to about 105° C. for a time sufficient for denaturation to occur which depend on the nucleic acid length, base content, and complementarity between single-strand sequences present in the sample, but typically about 0.5 to 4 minutes.

The thermostable enzyme preferably has optimum activity at a temperature higher than about 40° C., e.g., 65°-80° C. At temperatures much above 42° C., DNA and RNA dependent polymerases, other than thermostable DNA polymerases, are inactivated. Thus, they are inappropriate for catalyzing high temperature polymerization reactions utilizing a DNA or RNA template. Previous RNA amplification methods require incubation of the RNA/primer mixture in the presence of reverse transcriptase at a 37°-42° C. prior to the initiation of an amplification reaction.

Hybridization of primer to template depends on salt concentration and composition and length of primer. Hybridization can occur at higher temperatures (e.g., 45°-70° C.), which are preferred when using a thermostable polymerase. Higher temperature optimums for the thermostable enzyme enable RNA transcription and subsequent amplification to proceed with greater specificity due to the selectively of the primer hybridization process. Preferably, the optimum temperature for reverse transcription of RNA ranges from about 55°-75° C., more preferably 65°-70° C.

The present invention provides a method for reverse transcription of an RNA template, having enhanced primer directed specificity, catalyzed by a thermostable DNA polymerase. The methods disclosed are improved over prior methods for the reverse transcription of RNA. These methods provide for the amplification of an RNA segment via an RNA/cDNA hybrid intermediate molecule. The hybrid molecule is a suitable template for amplification by PCR. Thus, the reverse transcription and amplification reactions are coupled. Only by the present invention are all of the enzymatic steps for RNA amplification catalyzed by a thermostable DNA polymerase. The advantages brought to PCR by the commercial availability of Taq polymerase, are now, by the methods disclosed herein, applicable to reverse transcription, RNA detection, and cDNA preparation.

DNA amplification procedures by PCR are well known and are described in U.S. Pat. No. 4,683,202. For ease of understanding the advantages provided by the present invention, a summary of PCR is provided. PCR requires two primers that hybridize with the double-stranded target nucleic acid sequence to be amplified. In PCR, this double-stranded target sequence is denatured and one primer is annealed to each strand of the denatured target. The primers anneal to the target nucleic acid at sites removed from one another and in orientations such that the extension product of one primer, when separated from its complement, can hybridize to the other primer. Once a given primer hybridizes to the target sequence, the primer is extended by the action a of DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a double-stranded DNA molecule comprising: a first strand which contains the sequence of the first primer, eventually followed by the sequence complementary to the second primer, and a second strand which is complementary to the first strand.

The target of amplification can be an RNA/DNA hybrid molecule. Similarly the target can be single-stranded or double-stranded. Although the PCR procedure described above assumed a double-stranded target, this is not a necessity. After the first amplification cycle of a single-stranded DNA target, the reaction mixture contains a double-stranded DNA molecule consisting of the single-stranded target and a newly synthesized complementary strand. Similarly, following the first amplification cycle of an RNA/cDNA target, the reaction mixture contains a double-stranded cDNA molecule and a duplicate of the original RNA/cDNA target. At this point, successive cycles of amplification proceed as described above. In the present methods, the target of amplification is a single-stranded RNA, and the first amplification cycle is the reverse transcription step.

As used herein the term "cDNA" refers to a complementary DNA molecule synthesized using a ribonucleic acid strand (RNA) as a template. The RNA may be mRNA, tRNA, rRNA, or another form of RNA, such as viral RNA. The cDNA may be single-stranded, double-stranded or may be hydrogen-bonded to a complementary RNA molecule as in an RNA/cDNA hybrid. Such a hybrid molecule would result from, for example, reverse transcription of an RNA template using a DNA polymerase.

The methods of the present invention provide means for obtaining cDNA from a desired RNA template wherein the desired end product is produced with greater specificity than by previous methods. Additionally, the present invention provides that cDNA synthesis can be coupled to amplification by PCR. These methods incorporate previously unknown properties of thermostable DNA polymerases. In the disclosed embodiments methods are provided which utilize Taq polymerase for reverse transcription of an mRNA encoding interleukin-1β. This embodiment should not be construed as a limitation of the present invention.

Thermostable polymerases are available from a number of sources. The enzyme may be a native or recombinant protein. A preferred thermostable enzyme is Taq polymerase. Taq is commercially available as a recombinant product or purified as native Taq from *Thermus aquaticus* (Perkin Elmer-Cetus). Recombinant Taq is designated as rTaq and native Taq is designated as nTaq. Native Taq is purified from *T. aquaticus*. Also preferred for practice of the present invention is Tth purified from *T. thermophilus* or recombinant Tth.

Other thermostable polymerases that have been reported in the literature will also find use in the practice of the methods described. Examples of these include polymerases extracted from the thermophilic bacteria *Bacillus stearothermophilus, Methanothermus fervidus, Thermus aquaticus, T. flavus, T. lacteus, T. rubens, T. ruber,* and *T. thermophilus*. In addition, thermostable polymerases isolated from the thermophilic archaebacteria include, for example, *Desulfurococcus mobilis, Methanobacterium thermoautotrophicum, Sulfolobus solfataricus, S. acidocaldarius,* and *Thermoplasma acidophilum.*

Modified thermostable polymerases may result from proteolytic degradation or may be produced from a truncated gene. These proteins are also useful in the practice of the present invention so long as they function to polymerize deoxyribonucleotide triphosphates using an RNA template.

Taq polymerase can be prepared as both a 94 kDa and 62 kDa enzyme. The 62 kDa polymerase is a processed form of the 94 kDa enzyme, resulting from proteolytic cleavage of the N-terminal region. The 62 kDa polypeptide is composed of approximately two-thirds of the carboxy-terminal portion the full length protein. Either form of the enzyme will function to reverse transcribe RNA as described herein. In addition to the N-terminal deletion, individual amino acid residues may be modified by oxidation, reduction, or other derivatization, or the protein may be cleaved to obtain fragments that retain activity.

Thus, modification to the primary structure itself by deletion, addition, or alteration of the amino acids incorporated into the sequence during translation can be made without destroying the high temperature DNA polymerase activity of the protein. Such substitutions or other alterations result in proteins useful in the methods of the present invention. The availability of DNA encoding these sequences provides the opportunity to modify the codon sequence to generate mutant protein forms also having reverse transcriptase activity.

In a reverse transcription reaction a primer hybridizes with the RNA to be transcribed. The primer may be oligo(dT) or another primer. Oligo(dT) hybridizes to the polyadenylation (polyA) sequence of mRNAs and provides a primer for cDNA synthesis from a heterogeneous population of mRNAs. Because most eukaryotic mRNA molecules contain a polyA sequence at the 3' end, an oligo(dT) primer has general utility in the present methods, for example, in the preparation of a cDNA library.

A primer comprising a sequence sufficiently complementary to a specific RNA target molecule may be used to prime synthesis of the first cDNA strand complementary to a specific desired RNA segment if present. The method of high temperature reverse transcription provides novel means for the detection of specific RNAs in a sample. This method is useful in a clinical setting to monitor, for example, retrovirus infection in children born to AIDS victims or to monitor the expression of diagnostic proteins.

Detection of the reverse transcribed or amplified products can be accomplished by any of a number of known means. Such means include, but are not limited to, hybridization with isotopic or non-isotopically labeled probes in, for example, a dot blot or electrophoretic format. A detection format may include a capture step, such as a solid support substrate and avidin-biotin label system. Detection may include quantitative analysis to monitor progress of, for example, an infection or response to a treatment regimen. Alternatively, detection may be for the purpose of cell typing.

Primers can be designed with convenient restriction enzyme recognition sequences located at or near the 5' end of the primer. In the formation of the cDNA transcript, so long as the 3' end of the primer is hydrogen-bonded to the target sequence, the resulting double-stranded cDNA molecule would contain a specific enzyme restriction recognition sequence. Following amplification, the restriction site could be used to facilitate other procedures, for example, cloning.

The product of RNA transcription by a thermostable DNA polymerase is an RNA/cDNA hybrid molecule. The RNA can then be removed by heat denaturation or by a number of other known ways such as alkali, heat, or enzyme treatment. The remaining cDNA strand can then serve as a template for polymerization of a self-complementary strand, providing a double-stranded cDNA molecule suitable for additional amplification or other manipulation. The second strand synthesis also requires a primer. A sequence specific primer can be introduced into the reaction mix to prime second strand synthesis. A thermostable DNA polymerase is also a suitable catalyst for polymerization of the second cDNA strand. Thus, double-stranded cDNA is the product of a simplified, one enzyme reaction.

In the practice of the present methods, a thermostable DNA polymerase provides an RNA/cDNA hybrid molecule. Following synthesis of the second cDNA strand, the resultant double-stranded cDNA molecule can serve a number of purposes. Such purposes include DNA sequencing, amplification by a polymerase chain reaction, or detection of a specific nucleic acid sequence. Specific primers useful for amplification of a segment of the cDNA can be added subsequent to reverse transcription. In the practice of the disclosed methods, it may be desirable to use a first set of primers to synthesize a specific cDNA molecule and a second nested set of primers to amplify a desired cDNA segment. All of these reactions are catalyzed by the same thermostable DNA polymerase.

DNA polymerases require a divalent cation for catalytic activity. Tabor and Richardson, 1989, *Proc. Natl. Acad. Sci. USA* 86:4076-4080, have reported that $Mn^{2+}$ can be substituted for $Mg^{2+}$ in DNA sequencing methods. These methods require a DNA template and T7 DNA polymerase or DNA polymerase I.

In a disclosed embodiment of the present invention buffers are provided which contain $Mn^{2+}$ for nucleic acid transcription from an RNA template. These buffers are improved over previous reverse transcription buffers and result in increased cDNA yields. It may be suitable to decrease the concentration of dNTPs present in the reverse transcription reaction mix when using a $Mn^{2+}$ buffer. However, this adjustment is not essential to the operability of the disclosed methods.

For reverse transcription, according to the present invention, the primer-template mixture is incubated with a thermostable polymerase under suitable polymerization conditions. These conditions are provided by a buffer containing a divalent cation, a monovalent cation, all four deoxyribonucleotide triphosphates (dNTPs), and a buffering agent. In the present embodiment, the divalent cation is $MgCl_2$ or $MnCl_2$ in a concentration ranging from 0.05 mM to 2 mM for $MnCl_2$ or 0.5 to 10 mM $MgCl_2$. Preferably, the divalent cation is $MnCl_2$ at a concentration between 0.8 and 1.4 mM. The monovalent cation may be supplied by KCl, between 1-100 mM.

A suitable buffering agent is Tris-HCl, pH 8.3, although the pH may be in the range 8.2-8.8. The Tris-HCl concentration is from 5-50 mM, although 10-20 mM is most preferred. Additionally, EDTA less than 0.5 mM may be present. Detergents such as Tween-20 ™ and Nonidet ™ P-40 are present in the enzyme diluent buffers. A final concentration of non-ionic detergent less than 1% is appropriate and will not interfere with polymerase activity. Deoxyribonucleotide triphosphates are added as solution of the disodium salts of dATP, dCTP, dGTP, and dTTP (dNTPs). In the present methods a final concentration in the range of 1-500 $\mu$M is suitable.

Once the sample containing RNA has been prepared and the suitable primer and salts have been added, the reaction is incubated with the thermostable DNA polymerase for 10-60 minutes. Usually, however, a reaction time of 20 to 30 minutes is suitable. In the practice of the present methods the reaction mix is incubation above 40° C., although a preferred temperature is 60°-75° C. At this temperature, the specificity of the primer-template annealing is enhanced over the annealing specificity at a lower temperature and the enzyme has higher activity at the elevated temperature. At this high temperature non-specific priming by either incorrect primer-template hybridization or degraded native DNA serving as templates is avoided.

The reverse transcription yields a single-stranded cDNA transcript or an RNA/cDNA duplex wherein the cDNA strand has a segment that comprises the sequence complementary to that of the target RNA template. The RNA template may be denatured from the cDNA product thus providing a template for continuous reverse transcription resulting in a excess of single-stranded cDNA molecules. This excess of single-stranded cDNA can be detected by standard probe hybridization techniques. Thus, the invention provides means for direct detection of target segments. The resulting nucleic acid products can be detected by a number of electrophoretic or chromatographic means. The use of a radiolabeled triphosphate is helpful in monitoring the extent of the reaction and the size of products formed, although this is not an essential component of the invention.

The reaction products are suitable for amplification by PCR. After the reverse transcription reaction, the sample is quenched on ice and EDTA is added to 10 mM final concentration. The addition of EDTA is not an essential step of the present invention. Following quenching on ice, the reaction may be adjusted to amplification buffering conditions, and the amplification reaction can be initiated following the addition of a second primer and a heat denaturation step as provided by known PCR methods. Alternatively, if EDTA is added, the reaction product can be phenol extracted and ethanol precipitated and used as a PCR template. As another alternative, the reaction mix is diluted with an appropriate PCR buffer to dilute the concentration of EDTA.

The methods provided have numerous applications, particularly in the field of molecular biology and medical diagnostics. The reverse transcriptase activity described provides a cDNA transcript from an RNA template. The methods provide production and amplification of DNA segments from an RNA molecule, wherein the RNA molecule is a member of a population of total RNA or is present in a small amount in a biological sample. Detection of a specific RNA molecule present in a sample is greatly facilitated by a thermostable DNA polymerase used in the methods described herein. A specific RNA molecule or a total population of RNA molecules can be amplified, quantitated, isolated, and, if desired, cloned and sequenced using a thermostable DNA polymerase as described herein.

The methods and compositions of the present invention are a vast improvement over prior methods of reverse transcribing RNA into a DNA product. These methods provide products for PCR amplification that are far superior to any previously available, when starting with an RNA template. The invention provides more specific and, therefore, more accurate means for detection and characterization of specific ribonucleic acid sequences, such as those associated with infectious diseases, genetic disorders, or cellular disorders.

Those skilled in the art will recognize that the compositions of the instant invention can be incorporated into kits. Thus, the invention relates to kits that contain a thermostable DNA polymerase as well as instructions describing the method for using the same for reverse transcribing RNA. In one embodiment such a kit may relate to the detection of at least one specific target RNA sequence in a sample. Such a kit would comprise, in addition to the elements listed above, a primer containing a sequence sufficiently complimentary to a specific target RNA sequence to hybridize therewith. Diagnostic kits for the amplification and detection of at least one specific RNA sequence in a sample may comprise a primer having a sequence sufficiently identical with the RNA target to hybridize with the first strand of cDNA synthesized and prime a second cDNA strand. Kits may contain, in addition to the components listed, the four deoxyribonucleotide triphosphates, suitable buffers as described herein, oligo(dT), RNAseH, linkers for cloning, as well as one or more restriction enzymes.

The following examples are offered by way of illustration only and should not be construed as intending to limit the invention in any manner.

EXAMPLE I

Materials and Methods

I. Substrates

A. RNA

RNA was synthesized in vitro using T7 RNA polymerase and a synthetic template, pAW106. The template, pAW106, contains a T7 promoter adjacent to a synthetically prepared DNA segment followed by a polyadenylation sequence. The RNA produced, referred to herein as cRNA, was purified by oligo(dT) chromatography. The purified material, 1060 bases in length, contained a portion of interleukin 1$\beta$ (IL-1$\beta$) mRNA sequence. The RNA concentration was 0.1 $\mu$g/$\mu$l which was equivalent to ~0.286 pmoles/$\mu$l.

B. DNA

A DNA template was provided as a control for monitoring the activity of DNA polymerase. A solution of activated salmon sperm DNA was prepared at a concentration of 2.5 $\mu$g/$\mu$l in 1X Buffer. The 1X Buffer comprised 1 mM Tris-HCl, pH 8.3, 5 mM KCl, and 50 $\mu$M EDTA. One reaction contained 6.25 $\mu$g of salmon sperm DNA template.

II. Oligonucleotide Primer

DM 156 was used to prime synthesis of a cDNA molecule from the pAW106 cRNA template. The primer is 24 bases in length and comprises the sequence;

TGGAGAACACCACTTGTTGCTCCA.

This sequence corresponds to a portion of the human IL-1$\beta$ gene and is complementary to human IL-1$\beta$ mRNA. The primer concentration was 100 pmol/$\mu$l.

III. Deoxyribonucleotide Triphosphates

The amount of reverse transcription product formed was monitored by the incorporation of $\alpha^{32}$P-dCTP. Therefore, a dNTP minus C stock was prepared comprising 2 mM dATP, 2 mM dTTP, and 2 mM dGTP. A 1 mM dCTP solution was prepared containing 100 $\mu$Ci $\alpha^{32}$P dCTP (New England Nuclear). Therefore, approximately $6.6 \times 10^5$ cpm represents $10^3$ pmoles dCTP incorporated. The dnTP minus C and dCTP solutions were combined to prepare a 5X dNTP stock mix containing 1 mM dATP, 1 mM dTTP, 1 mM dGTP, and 250 $\mu$M $\alpha^{32}$P dCTP.

IV. Buffers

A. Annealing Buffer

The 10X stock annealing buffer was prepared containing 100 mM Tris-HCl pH 8.3, 500 mM KCl and 1 mM EDTA.

B. Modified Pol I 10X Buffer

The 10X Pol I buffers were prepared with and without MgCl$_2$ containing 100 mM Tris-HCl, pH 8.3, 500 mM KCl, 10 mM DTT, and 60 mM MgCl$_2$ if present.

C. Taq Polymerase/Reverse Transcription 10X Buffer (HSB)

The 10X Taq buffer was prepared containing 100 mM Tris-HCl, pH 8.3 and 500 mM KCl.

D. 10X Low Salt Buffer (LSB)

The 10X LSB was prepared containing 100 mM Tris-HCl, pH 8.3 and 50 mM KCl.

E. MuLV Reverse Transcriptase 10X Buffer

The 10X MuLV reverse transcriptase buffer was prepared as in C, above, with the addition of 60 mM MgCl$_2$.

F. Taq Diluent

Taq dilution buffer was prepared comprising: 25 mM Tris-HCl, pH. 8.8, 100 mM KCl, 0.1 mM EDTA, 0.1% Tween-20 TM, 0.1% Nonidet TM P-40, and 500 $\mu$g/ul gelatin.

V. Enzymes

A. Reverse Transcriptase (Murine Leukemia Virus RT) was obtained from Bethesda Research Labs, Bethesda, Md. at a concentration of 200 u/$\mu$l. The enzyme was diluted in 0.1% Tween-20 TM /Nonidet TM P-40 to provide 4 u/$\mu$l, 0.4 u/$\mu$l, 0.04 u/$\mu$l, and 0.004 u/$\mu$l preparations.

B. Taq (94 kDa) was provided by Perkin-Elmer/Cetus at a concentration of 48 units/$\mu$l. The specific activity was approximately 240,000 units/mg. Taq diluent was used to reduce the concentration to 10 units/$\mu$l.

C. 62 kDa Taq

Sixty-two kDa Taq is a truncated form of 94 kDa Taq in which the 32 kDa amino terminal sequence has been deleted. The enzyme can be produced in and purified from recombinant host cells as described in commonly assigned, co-pending U.S. Ser. No. 143,441, incorporated herein by reference, filed Jan. 12, 1988, and now abandoned in favor of continuation application Ser. No. 381,174, filed Jul. 28, 1989, that is in turn now abandoned in favor of application Ser. No. 07/971,798, filed Nov. 5, 1992.

D. Tth Polymerase

Tth polymerase is commercially available from Finnzyme Co., Finland, and from Toyobo Co., Japan. Methods for purifying and producing Tth by recombinant means are described in commonly assigned, co-pending U.S. Ser. No. 455,967, filed herewith at even date now abandoned in favor of continuation application Ser. No. 07/880,478, filed on May 6, 1992, and published as WO 91/09950and incorporated herein by reference.

E. E. coli Pol I was purchased from New England Biolabs at a concentration of 10 units/$\mu$l.

VI. Annealing Procedure

The cRNA template and DM156 primer were annealed at a 20:1 primer:template ratio in 1X annealing buffer. To reduce pipeting errors and eliminate tube variations, a master mix was made to provide material for 80 reactions.

Annealing was accomplished as follows: the 80X reaction mix was heated to 85°–87° C. for 4 minutes, then placed in a 70° C. water bath for 5 minutes, followed by a 60° C. water bath for 5 minutes and finally allowed to equilibrate at room temperature. The annealed mixture was then stored at 4° C. (or alternatively at −20° C.) for future use. For each reaction 2.5 $\mu$l of master mixture was used containing 0.5 pmol (0.175 $\mu$g) cRNA template and 10 pmoles primer.

VII. Determination of $\alpha P^{32}dCTP$ Incorporation

The amount of isotope incorporated in the reverse transcribed product was measured by nucleic acid precipitation with trichloroacetic acid (TCA). This method is described in Maniatis et al., 1982, *Molecular Cloning*, Cold Spring Harbor Laboratory, page 473.

EXAMPLE II

Analysis of AW106 cRNA as a Suitable Template for Reverse Transcription

The annealed AW106 cRNA:DM156 mixture was used as a template for reverse transcription with commercially available reverse transcriptase to test the suitability of AW106 cRNA as a template.

A 6X reaction mix was prepared containing 1X Pol I RT Buffer plus MgCl$_2$, 1X dNTP Stock, and 3 pmoles template annealed to 60 pmoles primer. This mix was aliquoted into six tubes. All reactions were set up at 0° C. As controls, one reaction was set up without template but with 10 units of MuLV reverse transcriptase. Another reaction had no enzyme added. To the remaining reactions, MuLV reverse transcriptase was added as follows: 10 units, 1 unit, 0.1 unit, and 0.01 unit.

All reactions were incubated at 37° C. for 20 minutes. The reactions were stopped by placing them in a 0° C. water ice/bath and adding EDTA to a final concentration of 10 mM. The $\alpha^{32}PdCTP$ incorporation was determined by measuring TCA precipitable counts.

The results demonstrated that AW106 cRNA was a suitable template of cDNA synthesis using MuLV reverse transcriptase.

EXAMPLE III

Comparison of *E. coli* Pol I and Taq Reverse Transcriptase Activities

Using the results of Example II as a standard, *E. coli* Pol I and Taq were assayed for reverse transcriptase activity using AW106 cRNA as a template. As positive controls, DNA templates were substituted for the cRNA template in one set of reactions. The results were quantitated as in Example II by measurement of $\alpha^{32}PdCTP$ incorporation.

A 12X Pol I master mix was prepared containing Pol I RT buffer minus MgCl$_2$ dNTP stock and 12 units Pol I enzyme. Similarly, a 12X Taq master mix was prepared containing Taq buffer, dNTP stock, and 12 units of Taq enzyme and Taq diluent. The Pol I and Taq master mixes were divided to provide six reactions for the RNA template (0.5 pmoles cRNA/10 pmole DM156), two reactions for the DNA template (6.25 $\mu$g), and two control reactions with no template.

For the RNA template MnCl$_2$ or MgCl$_2$ was added to the six aliquots containing Pol I master mix plus cRNA/DM156 to achieve salt concentrations of 0, 0.5 mM MnCl$_2$, 0.7 mM MnCl$_2$, 1.0 mM MnCl$_2$, 2.0 mM MnCl$_2$, and 6 mM MgCl$_2$. Six aliquots containing Taq master mix plus cRNA/DM156 were supplemented with MnCl$_2$ or MgCl$_2$ so that the final salt concentration was 0, 05 mM MnCl$_2$, 0.7 mM MnCl$_2$, 1.0 mM MnCl$_2$, 2.0 mM MnCl$_2$, and 2 mM MgCl$_2$.

For the DNA template two aliquots were removed from the Pol I mix, and salt was added as to provide a final concentration of 0.7 mM MnCl$_2$ for one reaction and 6 mM MgCl$_2$ for the other. Two aliquots were removed from the Taq mix, and salt was added to provide a final concentration of 0.7 mM MnCl$_2$ for one reaction and 2 mM MgCl$_2$ for the other.

As negative controls, two reaction mixes were prepared for each of Pol I and Taq which lacked a template. These reactions were assembled using aliquots of the 12X Pol I and 12X Taq master mixes, and 1X annealing buffer was added in place of a template. For Pol I, salt was added to provide either 0.7 mM MnCl$_2$ or 6 mM MgCl$_2$. For Taq, salt was added to provide either 0.7 mM MnCl$_2$ or 2 mM MgCl$_2$.

All reactions were mixed on ice and then incubated at 37° C. for Pol I or at 65° C. for Taq. After 20 minutes the reactions were chilled on ice (0° C.) and EDTA was added to each reaction to a 10 mM final concentration. A sample was removed from each reaction to measure $\alpha P^{32}dCTP$ incorporation.

The results of this experiment are shown in Table I. All values shown are corrected for background.

TABLE I

|  | CPM |
|---|---|
| MuLV Reverse Transcriptase | |
| minus template + 10 units enzyme | 90 |
| minus enzyme + template | 14 |
| 10 units enzyme + template | 7825 |
| 1 unit enzyme + template | 3263 |
| .1 unit enzyme + template | 924 |
| .01 unit enzyme + template | 170 |
| Taq Polymerase | |
| RNA template + 0 mM MnCl$_2$ | 9 |
| RNA template + .5 mM MnCl$_2$ | 256 |
| RNA template + .7 mM MnCl$_2$ | 3088 |
| RNA template + 1 mM MnCl$_2$ | 3977 |
| RNA template + 2 mM MnCl$_2$ | 2696 |
| RNA template + 2 mM MgCl$_2$ | 737 |
| minus template + .7 mM MnCl$_2$ | 5 |
| minus template + 2 mM MgCl$_2$ | 3 |
| DNA template + .7 mM MnCl$_2$ | 194,199 |
| DNA template + 2 mM MgCl$_2$ | 209,559 |
| *E. Coli* Pol I | |
| RNA template + 0 mM MnCl$_2$ | 0 |
| RNA template + .5 mM MnCl$_2$ | 7561 |
| RNA template + .7 mM MnCl$_2$ | 6666 |
| RNA template + 1 mM MnCl$_2$ | 7508 |
| RNA template + 2 mM MnCl$_2$ | 1558 |
| RNA template + 6 mM MgCl$_2$ | 760 |
| minus template + .7 mM MnCl$_2$ | 28 |

TABLE I-continued

|  | CPM |
|---|---|
| minus template + 6 mM MgCl$_2$ | 31 |
| DNA template + .7 mM MnCl$_2$ | 203,861 |
| DNA template + 6 mM MgCl$_2$ | 271,595 |

Figure 1:
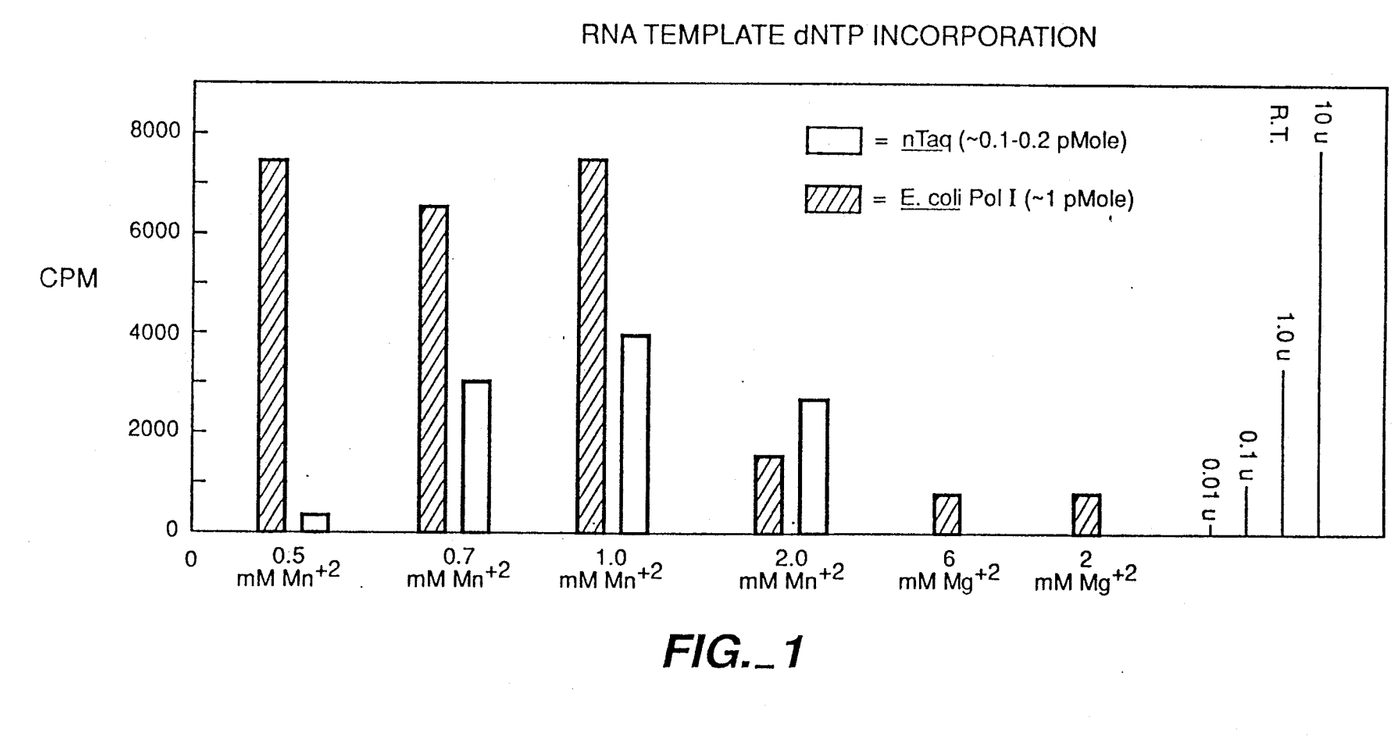
FIG. 1 is a graph comparing reverse transcriptase activity of *E. coli* Pol I, Taq and MuLV reverse transcriptase in MgCl$_2$ and MnCl$_2$ buffers.

The data presented in Table I is presented graphically in FIG. 1.

This experiment demonstrates that Taq has reverse transcriptase activity. One unit of Taq is equivalent to 1 unit of MuL V reverse transcriptase by the amount of $\alpha^{32}$PdCTP incorporated into a DNA transcript from an RNA template. *E. coli* Pol I also shows reverse transcriptase activity. Because Taq reactions were done at 65° C. rather than 37° C., product specificity is enhanced in the Taq reactions compared to either the Pol I or MuL V reverse transcriptase.

EXAMPLE IV

Comparison of Reverse Transcriptase Activity in 94 kDa rTaq, 62 kDa rTaq and Tth Polymerase In order to determine whether the reverse transcriptase activity observed in Example III was common to other thermostable polymerase, the following experiment was done. This experiment compares the reverse transcription activity of the full length Taq polymerase (94 kDa) with the truncated 62 kDa Taq and the full length thermostable polymerase isolated from *Thermus thermophilus* (Tth). Both forms of Taq were produced by recombinant means.

A 2 µM dilution of 94 kDa Taq was prepared, assuming 94 µg/nmole, from a 23.4 µmolar stock solution. A dilution of 62 kDa Taq was similarly prepared using Taq diluent.

Both the 94 kDa and 62 kDa dilutions contained 0.36 pmoles/0.18 µl. Tth polymerase was purified as a 27 unit/µl solution with a specific activity of 80,000 units/mg. Therefore, 0.1 µl contained 0.36 pmole (2.7 units of enzyme). Reaction were set up with a final salt concentration of 60 mM KCl (HSB) or 15 mM KCl (LSB).

At 0° C. three 15X master mixes were prepared containing dNTP stock, enzyme diluent, and 5.4 pmoles enzyme (Tth, 94 kDa Taq, or 62 kDa Taq). From each 15X master mix six aliquots were combined with either HSB or LSB providing six reaction mixes for each of Tth/HSB, Tth/LSB, 94 kDa Taq/HSB, 94 kDa Taq/LSB, 62 kDa Taq/HSB, and 62 kDa Taq/LSB.

For each of the six reaction mixes two separate aliquots were removed to tubes containing 1X annealing buffer for the minus template plus enzyme control reactions.

To the remaining five reactions worth of reaction mix, cRNA/DM156 annealed mix (3 pmoles template and 60 pmoles primer) was added. From each of the six series, four aliquots were removed to individual tubes. While still at 0° C., MnCl$_2$ was added to provide the final salt concentration show in Table II.

To determine background levels, minus-enzyme, minus-template controls were prepared containing 1X dNTP stock, 1X Annealing buffer, and 0.1X Taq diluent. The salts were adjusted as follows: HSB and a final MnCl$_2$ concentration of 0.6 mM or 1.2 mM, LSB and a final MnCl$_2$ concentration of 0.6 mM or 1.2 mM.

All reaction mixes were incubated at 65° C. for 15 minutes. The tubes were then quenched in an ice bath and EDTA was added to each tube to a 10 mM final concentration. The amount of $^{32}$PdCTP incorporation was determined by TCA precipitation. The results are shown in Table II.

TABLE II

|  |  | [MnCl$_2$] | CPM | pMoles |
|---|---|---|---|---|
| I. | 94 kDA rTaq |  |  |  |
|  | HSB |  |  |  |
|  | Minus template | .6 | 0 | — |
|  | Minus template | 1.2 | 0 | — |
|  | Plus template | .6 | 517 | 5.04 |
|  | Plus template | .8 | 918 | 8.96 |
|  | Plus template | 1.0 | 1315 | 12.83 |
|  | Plus template | 1.2 | 1305 | 12.73 |
|  | LSB |  |  |  |
|  | Minus template | .6 | 7 | — |
|  | Minus template | 1.2 | 18 | — |
|  | Plus template | .6 | 276 | 2.69 |
|  | Plus template | .8 | 1115 | 10.88 |
|  | Plus template | 1.0 | 1349 | 13.16 |
|  | Plus template | 1.2 | 1061 | 10.35 |
| II. | 62 kDa Taq |  |  |  |
|  | HSB |  |  |  |
|  | Minus template | .6 | 0 | — |
|  | Minus template | 1.2 | 0 | — |
|  | Plus template | .6 | 34 | .332 |
|  | Plus template | .8 | 340 | 3.32 |
|  | Plus template | 1.0 | 521 | 5.08 |
|  | Plus template | 1.2 | 609 | 5.9 |
|  | LSB |  |  |  |
|  | Minus template | .6 | 0 | — |
|  | Minus template | 1.2 | 0 | — |
|  | Plus template | .6 | 81 | .79 |
|  | Plus template | .8 | 468 | 4.57 |
|  | Plus template | 1.0 | 1068 | 10.46 |
|  | Plus template | 1.2 | 898 | 8.76 |
| III. | Tth Pol |  |  |  |
|  | HSB |  |  |  |
|  | Minus template | .6 | 10 | — |
|  | Minus template | 1.2 | 6 | — |
|  | Plus template | .6 | 1244 | 12.14 |
|  | Plus template | .8 | 1981 | 19.33 |
|  | Plus template | 1.0 | 2178 | 21.25 |
|  | Plus template | 1.2 | 2369 | 23.11 |
|  | LSB |  |  |  |
|  | Minus template | .6 | 234 |  |
|  | Minus template | 1.2 | 2 |  |
|  | Plus template | .6 | 618 | 6.03 |
|  | Plus template | .8 | 2363 | 23.06 |
|  | Plus template | 1.0 | 2239 | 21.85 |
|  | Plus template | 1.2 | 2051 | 20.01 |

| Controls Minus Enzyme, Minus Template Reactions | cpm |
|---|---|
| 60 mM KCl .6 mM MnCl$_2$ | 19 |
| 60 mM KCl 1.2 mM MnCl$_2$ | 46 |
| 15 mM KCl .6 mM MnCl$_2$ | 11 |
| 15 mM KCl 1.2 mM MnCl$_2$ | 25 |

Input $^{32}$P for each reaction was $1.23 \times 10^6$ cpm. All numbers were corrected for average background of 37 cpm. The numbers above are cpm incorporated per 12.5 µl of each reaction. Total pmoles of incorporation was calculated based on 984 cpm/mole determined by counting $^{32}$P strands from a $\alpha^{32}$P-dCTP stock solution.

Figure 2:
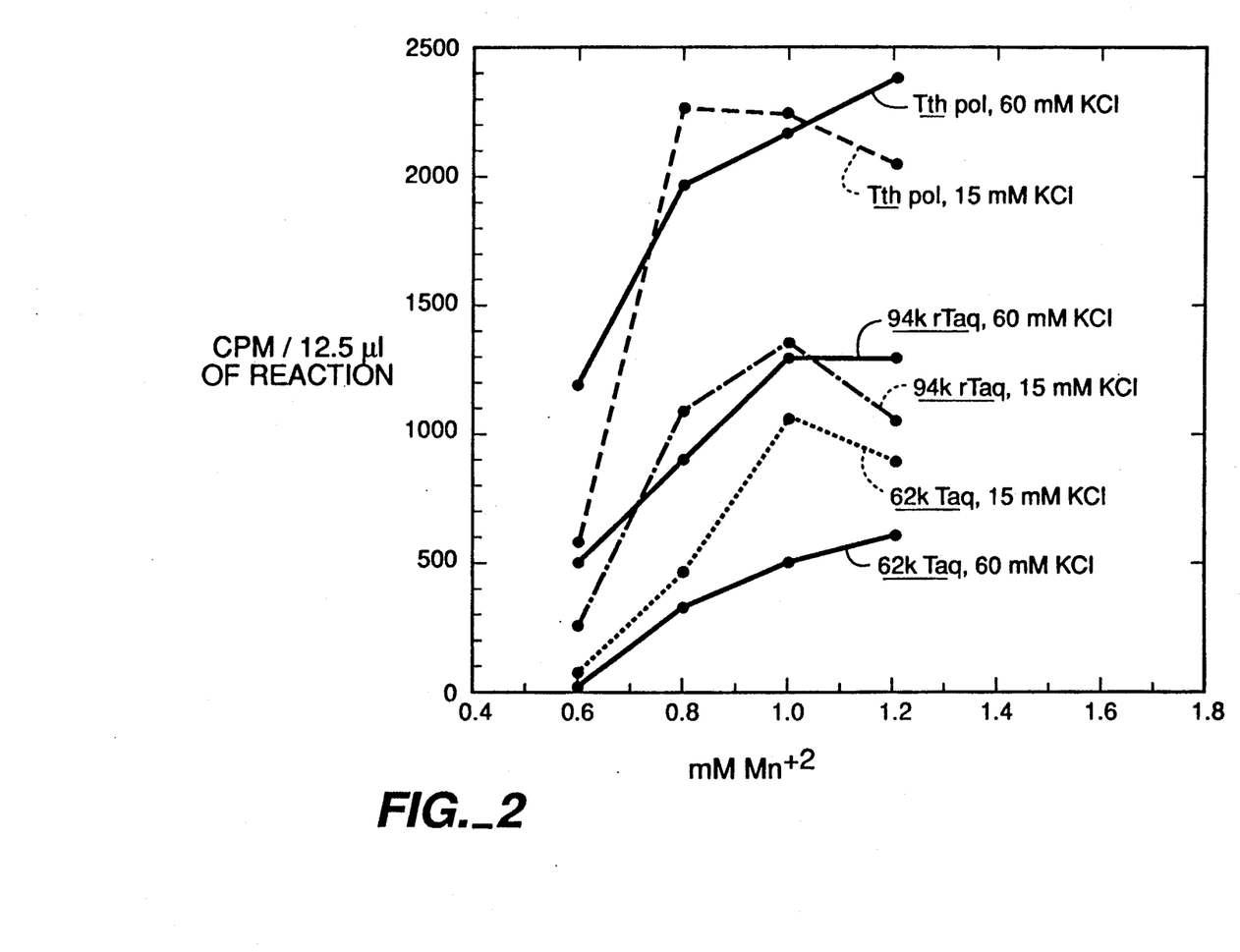
FIG. 2 is a graph comparing Tth, 94 kDa rTaq, 62 kDa rTaq catalyzed reverse transcription at varying Mg$^{2+}$ and Mn$^{2+}$ concentrations.

These results are presented graphically in FIG. 2 and demonstrate that all thermostable DNA polymerases tested contain reverse transcriptase activity.

The invention has been described in detail, but it will be understood that variations and modifications can be effected within the spirit and scope of the following claims.

I claim:

1. The method for reverse transcribing an RNA template that comprises treating a sample containing said RNA template with an oligonucleotide primer, which primer is sufficiently complementary to said RNA template to hybridize therewith, and a thermostable DNA polymerase having reverse transcriptase activity in the presence of all four deoxyribonucleotide triphosphate, in an appropriate buffer and at a temperature sufficient for said primer to hybridize to said RNA template and said thermostable DNA polymerase to catalyze the polymerization of said deoxyribonucleoside triphosphates to provide cDNA complementary to said RNA template.

2. A method according to claim 1 wherein said thermostable DNA polymerase having reverse transcriptase activity is Taq polymerase.

3. A method according to claim 2 wherein said temperature is between 50° C. and 80° C.

4. A method according to claim 3 wherein said buffer comprises a divalent cation from the group consisting of $Mg^{2+}$ and $Mn^{2+}$.

5. A method according to claim 4 wherein said divalent cation if $Mn^{2+}$ at a concentration of between about 0.5 and 2.0 mM.

6. The method of claim 2 wherein said sample is a human biological sample.

7. The method of claim 6 wherein said primer is complementary to a specific RNA target molecule.

8. The method of claim 7 wherein said specific RNA target molecule encodes a cytokine.

9. The method of claim 8 wherein said cytokine is IL-δ1.

10. The method of claim 7 wherein said specific RNA target molecule is diagnostic of a genetic or infectious disease.

11. A method for deleting a specific target RNA molecule in a sample suspected of containing said target RNA that comprises the step of:
(a) treating said sample with an oligonucleotide primer, which primer is sufficiently complementary to said target RNA to hybridize therewith, and a thermostable DNA polymerase having reverse transcriptase activity in the presence of all four deoxyribonucleotide triphosphate, in an appropriate buffer and at a temperature sufficient for said primer to hybridize to said target RNA and said thermostable DNA polymerase to catalyze the polymerization of said deoxyribonucleoside triphosphates to provide a cDNA sequence complementary to said target RNA;
(b) treating said cDNA formed in step (a) to provide a single-stranded cDNA and a RNA template; and
(c) determining whether said cDNA is present.

12. The method for claim 11 wherein said thermostable DNA polymerase having reverse transcriptase activity is Taq polymerase.

13. The method of claim 12 that further comprises after step (b) and before step (c); repeating steps (a) and (b) at least once.

14. The method of claim 12 wherein said specific RNA target molecule is diagnostic of a genetic or infectious disease.

15. A method for amplifying a target RNA molecular suspected of being present in a sample, the method comprising the steps of:
(a) treating said sample with a first primer, which primer is sufficiently complementary to said target RNA to hybridize therewith, and a thermostable DNA polymerase having reverse transcriptase activity in the presence of all four deoxyribonycleoside triphosphates, in an appropriate buffer and at a temperature sufficient for said first primer to hybridize with said target RNA and said thermostable DNA polymerase to catalyze to polymerization of said deoxyribonucleoside triphosphates to provide cDNA complementary to said target RNA;
(b) treating said cDNA formed in step (a) to provide single-stranded cDNA;
(c) treating said single-stranded cDNA formed in step (b) with a second primer, wherein said second primer can hybridize to said single-stranded cDNA molecule and initiate synthesis of an extension product in the presence of a thermostable DNA polymerase under appropriate conditions to produce a double-stranded cDNA molecule; and
(d) amplifying the double-stranded cDNA molecule of step (c) by a polymerase chain reaction.

16. The method for RNA amplification of claim 15 wherein said thermostable DNA polymerase having reverse transcriptase activity is Taq polymerase.

17. The method of claim 16 wherein said RNA target is diagnostic of a genetic or infectious disease.

18. A method for preparing duplex cDNA from an RNA template that comprises the steps of:
(a) treating said RNA template with a first primer, which primer is sufficiently complementary to said RNA template to hybridize therewith, and a thermostable DNA polymerase having reverse transcriptase activity in the presence of all four deoxyribonucleoside triphosphates, in an appropriate buffer and at a temperature sufficient for said first primer to hybridize with said RNA template and said thermostable DNA polymerase to catalyze the polymerization of said deoxyribonucleoside triphosphates to provide cDNA complementary to said target RNA;
(b) treating said cDNA formed in step (a) to provide single-stranded cDNA;
(c) treating said single-stranded cDNA formed in step (b) with a second primer, wherein said second primer can hybridize to said single-stranded cDNA molecule and initiate synthesis of an extension product in the presence of a thermostable DNA polymerase under appropriate conditions to produce a double-stranded cDNA molecule.

* * * * *

UNITED STATES PATENT AND TRADEMARK OFFICE
CERTIFICATE OF CORRECTION

PATENT NO. : 5,322,770

DATED : June 21, 1994

INVENTOR(S) : David H. Gelfand

It is certified that error appears in the above-identified patent and that said Letters Patent is hereby corrected as shown below:

In Claim 1, column 17, line 4, please delete "deoxyribonucleotide" and insert therefor --deoxyribonucleoside--.

In Claim 1, column 17, line 4, please delete "triphosphate" and insert therefor --triphosphates--.

In Claim 5, column 17, line 20, please delete "if" and insert therefor --is--.

In Claim 9, column 17, line 29, please delete "IL-δ1" and insert therefor --IL-β1--.

In Claim 11, column 17, line 33, please delete "deleting" and insert therefor --detecting--.

In Claim 11, column 17, line 41, please delete "deoxyribonucleotide" and insert therefor --deoxyribonucleoside--.

In Claim 11, column 17, line 41, please delete "triphosphate" and insert therefor --triphosphates--.

UNITED STATES PATENT AND TRADEMARK OFFICE
CERTIFICATE OF CORRECTION

PATENT NO. : 5,322,770
DATED : June 21, 1994
INVENTOR(S) : David H. Gelfand

It is certified that error appears in the above-indentified patent and that said Letters Patent is hereby corrected as shown below:

In Claim 15, column 18, line 11, please delete "deoxyribony-" and insert therefor --deoxyribonu--.

Signed and Sealed this

Eleventh Day of April, 1995

Attest:

BRUCE LEHMAN

Attesting Officer        Commissioner of Patents and Trademarks